US009295207B2

(12) United States Patent
Linders et al.

(10) Patent No.: US 9,295,207 B2
(45) Date of Patent: Mar. 29, 2016

(54) **CLUBROOT RESISTANCE *BRASSICA OLERACEA* PLANTS**

(75) Inventors: Enrico Gerardus Albertus Linders, Enkhuizen (NL); Peter Tjeertes, Enkhuizen (NL); Johannes Maria De Haas, Enkhuizen (NL); Cai-Cheng Huang, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 13/114,176

(22) Filed: May 24, 2011

(65) Prior Publication Data

US 2011/0231951 A1 Sep. 22, 2011

Related U.S. Application Data

(60) Continuation of application No. 12/573,963, filed on Oct. 6, 2009, now Pat. No. 8,013,209, which is a division of application No. 10/522,094, filed as application No. PCT/EP03/08197 on Jul. 25, 2003, now abandoned.

(30) Foreign Application Priority Data

Jul. 26, 2002 (GB) .................................. 0217406.8

(51) Int. Cl.
*A01H 1/02* (2006.01)
*A01H 1/04* (2006.01)
*A01H 4/00* (2006.01)
*A01H 5/10* (2006.01)

(52) U.S. Cl.
CPC ... *A01H 1/04* (2013.01); *A01H 5/10* (2013.01)

(58) Field of Classification Search
USPC ........................................ 800/260, 265, 269
See application file for complete search history.

(56) References Cited

U.S. PATENT DOCUMENTS 5,254,802 A 10/1993 Hoekstra et al.

FOREIGN PATENT DOCUMENTS

WO WO 00/55340 9/2000
WO WO 03/000898 1/2003

OTHER PUBLICATIONS

Chiang et al. HortScience 20(3): 457-458, 1985.*
Bradshaw et al. Ann. Appl. Biol. 130: 337-348, 1997.*
Ludwig-Muller et al. Phytochemistry 44(3): 407-414, 1997.*
Bradshaw et al (Ann. Appl. Biol. 130: 337-348, 1997).*
Ludwig-Muller et al (Phytochemistry 44(3): 407-414, 1997).*
Yoshikawa (Japan Agricultural Research Quarterly 17(1): 6-11, 1983).*
Botstein et al., The American Journal of Human Genetics, 1980, 32, pp. 314-331.
Bradshaw et al., Annals of Applied Biology, 1997, 130, pp. 337-348.
Buczacki et al., Transactions of the British Mycological Society, 1975, 65, 2, pp. 295-303.
Chang et al., Database GSN Online, Nov. 20, 2003; Rice gene SEQ ID No. 4190, Accession No. ADA70867.
Chiang et al., Canadian Journal of Plant Science, Jan. 1989, 69, pp. 337-340.
Chiang et al., Euphytica, 1979, 28, pp. 41-45.
Chiang et al., Euphytica, 1983, 32, pp. 479-483.
Dixon et al., Acta Horticulturae, 1998, 459, pp. 343-350.
Dixon, Grower, Apr. 29, 1999, pp. 28-29.
Fehr, Iowa State University, "Principles of Cultivar Development," vol. 1 Theory and Technique, (Macmillian Pubishing Co., New York, 1987) pp. 360-376.
Gowers, Euphytica, 1982, 31, pp. 971-976.
Harberd, Euphytica, 1969, 18, pp. 425-429.
Hearne et al., Trends in Genetics, 1992, 8, 8, pp. 288-294.
Inomata, Monographs on Theoretical and Applied Genetics, 1993, 19, pp. 94-107.
JP 09 117284 A (Yasai Chagyo Shikenbacho) May 6, 1997 (abstract) World Patents Index [online] London, U.K.: Derwent Publications, Ltd., XP002264817, Accession No. 1997-305513.
Konieczny et al., The Plant Journal, 1993, 4, 2, pp. 403-410.
KR 010 006 352 A (Univ. Chungnam Nat) Aug. 14, 2002 (abstract) World Patents Index [online] London, U.K.: Derwent Publications, Ltd., XP002264818, Accession No. 2003-145043.
Landry et al., Genome, 1992, 35, 3, pp. 409-420.
Makaroff et al., The Journal of Biological Chemistry, 1989, 264, 20, pp. 11706-11713.
Matsumoto Etsuo et al., Euphytica, 1998, 104, 2, pp. 79-86.
Michaels et al., The Plant Journal, 1998, 14, 3, pp. 381-385.
Neff et al., The Plant Journal, 1998, 14, 3, pp. 387-392.
Ogura, Memoirs of the Faculty of Agriculture (Kagoshima University, Kagoshima, Japan, The Faculty of Agriculture, Feb. 1968), vol. VI, No. 2, pp. 39-78.
Poehlman et al. "Backcross breeding" in Breeding Field Crops Fourth Edition (Iowa State Press, 1995), pp. 172-175.
Robinson, R.A., Review Applied Mycology, Nov.-Dec. 1969, 48, 11-12, pp. 593-606.
Sigareva et al., Theoretical and Applied Genetics, 1997, 94, pp. 213-220.
Song et al., Theoretical and Applied Genetics, 1988, 75, pp. 784-794.
Song et al., Theoretical and Applied Genetics, 1998, 76, pp. 593-600.
Voorrips et al., Theoretical and Applied Genetics, 1997, 94, pp. 75-82.
Voorrips et al., Euphytica, 1995, 83, pp. 139-146.
Williams et al., Nucleic Acids Research, 1990, 18, 22, pp. 6531-6535.
Yoshikawa, H., Japan Agricultural Research Quarterly, 1973, 17, 1, pp. 6-11.
Crisp et al., Euphytica, 1989, 42, pp. 215-226.
Hu et al., Genome, 1998, 41, pp. 226-235.
Chiang et al., Hortscience, 1989, 24, 4, pp. 665-666.
Chiang et al., Euphytica, 1980, 29, pp. 47-55.
Kuginuki et al., European Journal of Plant Pathology, 1999, 105, pp. 327-332.
Kuginuki et al., Euphytica, 1997, 98, pp. 149-154.
Nishi, "Hakuran, an Interspecific Hybrid Between Chinese Cabbage and Common Cabbage," in Chinese Cabbage, Proc of the First Int Symposium, Tsukuba, Japan, 1981, pp. 385-391.
Yoshikawa, "Breeding for Clubroot Resistance in Chinese Cabbage," in Chinese Cabbage, Proc of the First Int Symposium, Tsukuba, Japan, 1981, pp. 405-413.

(Continued)

*Primary Examiner* — Keith Robinson
(74) *Attorney, Agent, or Firm* — Karen A. Magri

(57) ABSTRACT

The present invention discloses *B. oleracea* plants resistant to clubroot disease. In particular, the plants of the present invention comprise a monogenic dominant resistance to the disease clubroot introgressed from *B. rapa*. This resistance provides improved resistance to the disease as compared to previously existing resistances in *B. oleracea*.

4 Claims, 1 Drawing Sheet

(56) References Cited

OTHER PUBLICATIONS

Matsuzawa, Japan J. Breeding, 1983, 33, 3, pp. 321-330.
Chiang et al., Hortscience, 1985, 20, 3, pp. 457-458.
Voorrips et al., Neth. J. Pl. Path., 1993, 99, pp. 269-276.
Baggett et al., Hortscience, 1985, 20, 4, pp. 784-785.
Ludwig-Miller, Phytochemistry, 1997, 44, 3, pp. 407-414.
Song et al., Theoretical and Applied Genetics, 1990, 79, pp. 497-506.
Toxopeus et al., Transaction of the British Mycological Society, 1986, 87, 2, pp. 279-287.
Ludwig-Muller et al., Phytochemistry, 1997, 44, 3, pp. 407-414.
Extract of Sluis & Groot "Quality Seeds" catalogue, 1994.
Extract of Takii Seed "Vegetable Catalog New and Standard Varieties", 1996, pp. 44-51.
Extract of S&G "European assortment Vegetable seeds" catalogue, 1999-2000.
Voorrips et al., Euphytica, 1997, 93, pp. 41-48.
File History for U.S. Appl. No. 12/573,963.
File History for U.S. Appl. No. 10/522,094.
Ostergaard, L. & King, G.J., Standardized gene nomenclature for the *Brassica* genus. Plant Methods, (May 20, 2008)., p. 1-4, 4:10; doi: 10.1 186/1746-4811-4-10; BioMedCentral Publishing.
Ayotte et al., "The transfer of triazine resistance form Brassica Napus L. to B. Oleracea L. I. production of F1 hybrids through embryo rescue," Euphytica36(1987):615-624.
Hansen and Earle, "Transfer of resistance to Xanthomonas campestris pv campestris into Brassica oleracea L. by protoplast fusion." Theor Appl Genet (1995), 91:1293-1300.
Hossain et al., "Seed vernalized interspecific hybrids through in vitro ovule culture in Brassica," Plant Science, 68(1990)95-102.
EPO Supplementary Search Report dated Oct. 19, 2010.
Third Party Observations dated Nov. 2, 2006.
Third Party Observations dated Jan. 27, 2010.
Third Party Observations dated Sep. 3, 2010.
Third Party Observations dated Jan. 14, 2011.
P.H. Williams, Sceening Crucifires for Multiple Disease Resistance, Crucifer Workshop, Sep. 1981, University of Wisconsin-Madison.
Triangle of U (Wikipedia).

\* cited by examiner

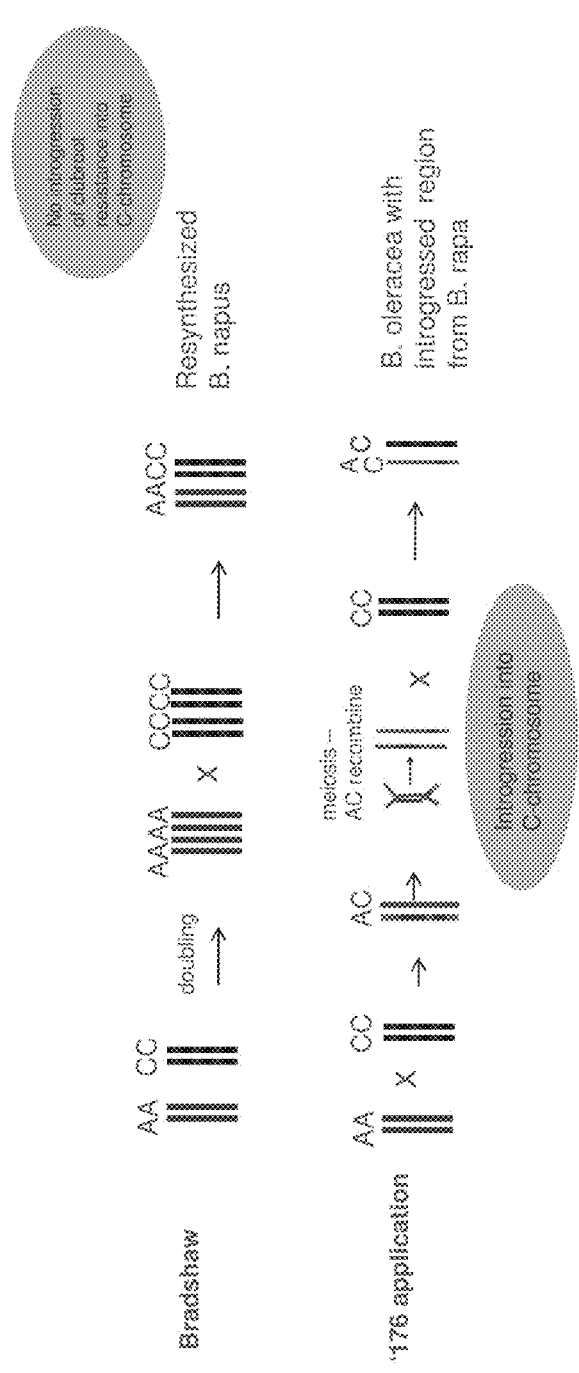

CLUBROOT RESISTANCE *BRASSICA OLERACEA* PLANTS

CROSS-REFERENCE TO RELATED APPLICATIONS

This application is a continuation of U.S. patent application Ser. No. 12/573,963, which is a divisional application of U.S. patent application Ser. No. 10/522,094, which is a national phase application of International application PCT/EP03/008197, filed Jul. 25, 2003, which claims priority to Great Britain Application No. 0217406.8, filed Jul. 26, 2002.

The present invention relates to plants resistant to diseases, in particular to *Brassica oleracea* plants resistant to the disease clubroot.

Clubroot is a widespread disease that causes serious problems in many *Brassica* growing areas (for a review see e.g. Dixon (1999) Grower April 29, pp. 28-29). The disease is caused by *Plasmodiophora brassicae*, a one-cellular organism. Symptoms of the disease include root malformations with hard swellings (clubs), that eventually rot. The disease also causes stunting through reduced growth, and wilting of leaves is observed under water stress. Chemical control of the disease is not effective. Therefore, good genetic resistance of the crop is important for its protection against the disease.

The genus of the *Brassicas* comprises several species of commercial interest, such as *B. rapa* (Chinese cabbage, pak choi, turnip), *B. napus* (oil seed, swede), *B. juncea* (mustard), *B. nigra* (black mustard) and *B. oleracea* (cauliflower, broccoli, cabbage, Brussels sprouts, savoy cabbage, borecole, kohl rabi, borecole and others). While sub-species within a species of the *Brassica* genus are usually sexually compatible, this is not necessarily the case between different species of the *Brassica* genus. For example, *B. rapa* and *B. oleracea* do not have the same number of chromosomes (10 chromosomes versus 9 chromosomes) and are therefore not sexually compatible. This renders the transfer of a trait from one *Brassica* species to another particularly difficult.

Several sources of resistance to clubroot have been described within the *Brassica* genus (see e.g. Bradshaw et al. (1997) Ann. Appl. Biol. 130:337-348; Gowers (1982) Euphytica 31:971-976). Some resistances are monogenic, some polygenic, some are dominant, some recessive. Monogenic dominant resistances have been described in *B. rapa* and *B. napus*, such as for example a monogenic dominant resistance in the *B. rapa* Chinese cabbage (Yoshikawa (1983) Japan Agricultural Research Quarterly, Vol. 17, no. 1, p. 6-11). Chinese cabbage F1-hybrids with this resistance have been shown to have good protection against clubroot, although a small number of strains ('races') of clubroot have been able to break through this resistance. Such races seem more prevalent in Asia than in Europe.

By contrast, only polygenic, recessive sources of resistance have been described in the *Brassica* species *B. oleracea* (see e.g. Voorrips (1995) Euphytica 83:139-146). Such sources have proven not only to be insufficiently resistant to clubroot, but they are also very difficult to transfer between commercial *B. oleracea* lines. This renders the breeding of the resistance a difficult and time consuming task.

Therefore, there is an unfulfilled need for *B. oleracea* plants with an improved resistance to clubroot, wherein the resistance is also easy to breed and transfer to commercial *B. oleracea* lines.

Accordingly, the present invention addresses the problem of unsatisfactory resistance to the disease clubroot in *B. oleracea*. To achieve improved resistance to the disease in *B. oleracea*, the present invention discloses the transfer of a monogenic dominant resistance to clubroot from chinese cabbage (*B. rapa*) to the *B. oleracea* broccoli, and then further to other *B. oleraceas*, such as white cabbage, cauliflower and Brussels sprouts. In order to overcome the sexual incompatibility between *B. rapa* and *B. oleracea*, the resistance to clubroot was transferred by means of interspecific hybridization using an embryo-rescue technique, followed by repeated backcrosses and disease tests in all backcross generations. High level of resistance to clubroot is obtained in the resulting *B. oleracea* plants. The resistance is stable, and can be transmitted to further generations and transferred to susceptible or less resistant *B. oleracea* plants.

Thus, the present invention discloses *B. oleracea* plants resistant to clubroot, wherein the resistance to clubroot is monogenic and dominant, including seeds and materials of said plants and the progeny thereof. The present invention also discloses methods to produce *B. oleracea* plants resistant to clubroot, methods to transfer the clubroot resistance to susceptible or less resistant *B. oleracea* plants. The present invention also further discloses molecular markers linked to the resistance to clubroot.

The present invention is particularly advantageous over existing resistances to clubroot in *B. oleracea* in that the resistance of the instant invention is easily transferred between *B. oleracea* plants and commercial lines. Higher yields are obtained because of the absence of disease on resistant plants. Moreover much less crop protection chemicals or no crop protection chemicals at all are required against clubroot when *B. oleracea* plants of the present invention are grown.

The present invention therefore discloses:

A *B. oleracea* plant resistant to clubroot disease, more particularly to clubroot disease caused by the pathogen *Plasmodiophora brassicae*. In a specific embodiment of the invention, the resistance to clubroot disease is monogenic and dominant. Preferably, the *B. oleracea* plant is rated at level 2 or less in a test for the disease having a 1-9 scale, preferably such as described in Example 2. Preferably, the *B. oleracea* plant is rated at level 1 in a test for the disease having a 1-9 scale, preferably such as described in Example 2. Preferably, the *B. oleracea* plant is rated at level 1 or less in a test for the disease having a 0-5 scale, preferably such as described in Example 2. Preferably, the *B. oleracea* plant is rated at level 0 in a test for the disease having a 0-5 scale, preferably such as described in Example 2. In another preferred embodiment, the *B. oleracea* plant is resistant to root hair infection. In another preferred embodiment, the *B. oleracea* plant is broccoli, white cabbage, cauliflower, Brussels sprouts, Borecole, Savoy, or red cabbage. In another preferred embodiment, the *B. oleracea* plant is homozygous or heterozygous for the resistance to clubroot. In another preferred embodiment, the resistance to clubroot is genetically linked to a molecular marker. Preferably, the molecular marker obtainable by PCR amplification. Preferably, the resistance is within 10 cM of said molecular marker, preferably within less than 6 cM, preferably within less than 5 cM, more preferably within less than 3 cM, even more preferably within less than 1.5 cM. In another preferred embodiment, the resistance to clubroot is linked to a molecular marker obtainable by PCR amplification using primer O20 (SEQ ID NO:1) or primer Y13 (SEQ ID NO:2). In another preferred embodiment, the resistance is obtainable from a clubroot resistant *B. rapa* plant, preferably from Chinese cabbage F1 hybrid Parkin. In another preferred embodiment, the resistance to clubroot according to the present invention is obtainable from line CFL667, deposited with NCIMB under accession number NCIMB 41134. In another preferred embodiment, the resistance is derived or obtained from line CFL667, or from a progeny or ancestor of line CFL667 comprising said resistance. In another preferred embodiment, the plant is an inbred or a hybrid. In another preferred embodiment, the plant is a dihaploid. In yet another preferred embodiment, the plant is cytoplasmic male sterile (CMS). In another preferred embodiment, the present invention discloses a B. oleracea plant comprising a locus conferring resistance to clubroot. Preferably, the locus is within 10 centi-Morgan (cM) of a molecular marker obtainable by PCR amplification using primer O20 (SEQ ID NO:1) or primer Y13 (SEQ ID NO:2), preferably within 6 cM, preferably within 5 cM, more preferably within 3 cM, even more preferably within 1.5 cM of said molecular marker. In another preferred embodiment, the resistance is at locus corresponding to the locus comprised in line CFL667, deposited with NCIMB under accession number NCIMB 41134, and preferably co-segregates with the resistance present in line CFL667. In another preferred embodiment, the locus conferring the resistance to clubroot is obtainable from line CFL667, deposited with NCIMB under accession number NCIMB 41134, or from a progeny or ancestor of line CFL667 comprising said resistance. In another preferred embodiment, the locus for the resistance is derived or obtained from line CFL667, or from a progeny or ancestor of line CFL667 comprising said resistance.

The present invention further discloses:

Seed of a plant disclosed above, including the progeny thereof, wherein said seed or progeny comprises the resistance of the present invention.

Fruit of a plant disclosed above. Part of a plant disclosed above, including pollen, ovule, and embryo of said plant.

The present invention further discloses:

A B. oleracea plant comprising a resistance to clubroot disease, wherein when said plant is homozygous for said resistance and said plant homozygous for said resistance is crossed with a "tester" plant homozygous for a monogenic and dominant resistance to clubroot disease, plants of the first generation progeny resulting from said cross show a 1:0 segregation for resistance to clubroot disease. In a preferred embodiment, when said plants of said first generation progeny are self-pollinated, plants of the resulting second generation progeny shows a 1:0 segregation for resistance to clubroot disease. In a preferred embodiment, the "tester" plant is a plant derived from line CFL667 deposited with NCIMB under accession number NCIMB 41134 and comprising the monogenic and dominant resistance to clubroot comprised in said line CFL667, or a progeny or ancestor of said line CFL667 comprising the monogenic and dominant resistance to clubroot comprised in said line CFL667. In a preferred embodiment, the "tester" plant is derived from a plant of line CFL667 or a progeny plant of line CFL667 by cell fusion. In another preferred embodiment, the "tester" plant is male fertile.

A B. oleracea plant comprising a resistance to clubroot disease, wherein when said plant is heterozygous for said resistance and said plant heterozygous for said resistance is crossed with a "tester" plant heterozygous for a monogenic and dominant resistance to clubroot, plants of the first generation progeny resulting from said cross show a 3:1 segregation for resistance to clubroot disease. In a preferred embodiment, when said plants of said first generation progeny are further crossed with said plant heterozygous for said resistance, plants of the resulting second generation progeny shows a 5:1 segregation for resistance to clubroot disease. In a further preferred embodiment, the "tester" plant is a plant of line CFL667 deposited with NCIMB under accession number NCIMB 41134, or a progeny or ancestor of said line CFL667 comprising the monogenic and dominant resistance to clubroot comprised in said line CFL667, or a plant derived from said line CFL667 deposited with NCIMB under accession number NCIMB 41134 and comprising the monogenic and dominant resistance to clubroot comprised in said line CFL667. In another preferred embodiment, when progenies of individual plants are scored, the resulting second generation progeny shows a 3:1, 1:0 or 1:1 segregation ratio for the resistance, depending on the genetic status of the individual plants in the first generation offspring (heterozygous, homozygous resistant or homozygous susceptible respectively).

In another preferred embodiment, said resistance to clubroot is monogenic, preferably monogenic and dominant. In a preferred embodiment, the B. oleracea plant is homozygous for the resistance. In another preferred embodiment, the B. oleracea plant is heterozygous for the resistance.

The present invention further discloses:

Seed of a plant disclosed above, including the progeny thereof, wherein said seed or progeny comprises the resistance of the present invention.

Fruit of a plant disclosed above. Part of a plant disclosed above, including pollen, ovule, and embryo of said plant.

The present invention further discloses:

Use of a monogenic and dominant resistance to clubroot according to the present invention to confer a B. oleracea plant resistance to said disease. Preferably, said resistance is obtainable from a B. rapa plant, preferably from Chinese cabbage F1 hybrid Parkin.

The present invention further discloses:

A method for producing a B. oleracea plant comprising a monogenic and dominant resistance to clubroot comprising the steps of: a) obtaining a B. rapa plant resistant to clubroot; b) crossing said B. rapa plant with a B. oleracea plant, c) rescuing embryos resulting from the cross of step b); d) regenerating a plant from a embryo of step c); e) selecting a plant of step d) that is resistant to clubroot; f) back-crossing a plant resulting from step e) with a B. oleracea plant. In a preferred embodiment, the method further comprises introgressing the resistance into an elite B. oleracea inbred. In another preferred embodiment, the method further comprises crossing said inbred to another B. oleracea inbred to produce a hybrid.

The present invention further discloses:

A B. oleracea plant, including a hybrid plant, obtainable by a method disclosed above.

The present invention further discloses:

A method for transferring a monogenic and dominant resistance to clubroot to a B. oleracea plant susceptible or less resistant to the disease comprising the steps of: a) obtaining a B. oleracea plant comprising a monogenic and dominant resistance to clubroot; b) crossing said B. oleracea plant of step a) with a B. oleracea plant susceptible or less resistant to clubroot; c) selecting a plant from the cross of step b) that is resistant to clubroot. In a preferred embodiment, the method further comprises backcrossing said resistance into said B. oleracea plant susceptible or less resistant to clubroot. In a preferred embodiment, a B. oleracea plant susceptible or less resistant to the disease is rated at level 4 or above, preferably 3 or above, in a test for the disease having a 1-9 scale, or at level 3 or above, preferably 2 or above, in a test for the disease having a 0-5 scale.

The present invention further discloses:

A DNA fragment amplified from a Brassica genome, wherein said DNA fragment is approximately 400 bp long and comprises SEQ ID NO:1.

A DNA fragment amplified from a *Brassica* genome, wherein said DNA fragment is approximately 640 bp long and comprises SEQ ID NO:2.

In a preferred embodiment, a DNA fragment disclosed above is indicative of the presence of a dominant and monogenic resistance to clubroot in a *Brassica* plant.

Use of a DNA fragment disclosed above to identify a *Brassica* plant that is resistant to clubroot.

Use of primer O20 (SEQ ID NO:1) to detect a DNA fragment of approximately 400 bp in a *Brassica* genome.

Use of primer Y13 (SEQ ID NO:2) to detect a DNA fragment of approximately 640 bp in a *Brassica* genome.

Use of a primer O20 or Y13 to identify a *Brassica* plant resistant to clubroot.

In a preferred embodiment, the *Brassica* plant is *B. oleracea*.

A kit for detecting a monogenic and dominant resistance to clubroot in a *B. oleracea* plant comprising an oligonucleotide as set forth in SEQ ID NO:1 or SEQ ID NO:2.

The present invention further discloses:

A method for transferring a monogenic and dominant resistance to clubroot to a *B. oleracea* plant susceptible or less resistant to the disease comprising the steps of: a) obtaining a *B. oleracea* plant comprising a monogenic and dominant resistance to clubroot; b) crossing said *B. oleracea* plant of step a) with a *B. oleracea* plant susceptible or less resistant to clubroot; c) selecting a plant comprising a DNA fragment obtainable by PCR amplification and which co-segregates with the resistance. Preferably, the DNA fragment is obtainable by PCR amplification using primer O20 (SEQ ID NO:1) or primer Y13 (SEQ ID NO:2). Preferably, said plant of step c) is resistant to clubroot. In a preferred embodiment, the method further comprises backcrossing said resistance into said *B. oleracea* plant susceptible or less resistant to clubroot.

The present invention further discloses:

A method of identifying a *B. oleracea* plant resistant to clubroot comprising the steps of: a) obtaining a sample from a *B. oleracea* plant; b) detecting in said sample a DNA fragment obtainable by PCR amplification using primer O20 (SEQ ID NO:1) or primer Y13 (SEQ ID NO:2), wherein said *B. oleracea* plant of step b) is resistant to clubroot.

The present invention further discloses:

A method of selecting a *B. oleracea* plant resistant to clubroot from a population of *B. oleracea* plants comprising the steps of: a) providing a population of *B. oleracea* plants; b) obtaining a sample of a plant of said population; c) detecting in said sample a DNA fragment obtainable by PCR amplification using primer O20 (SEQ ID NO:1) or primer Y13 (SEQ ID NO:2), wherein said *B. oleracea* plant of step b) is resistant to clubroot.

DEFINITIONS

Trait: characteristic or phenotype, for example a resistance to a disease. A trait may be inherited in a dominant or recessive manner, or may be monogenic or polygenic. A trait is for example a resistance to a disease, such as clubroot.

Resistance: characteristic or phenotype of a plant to exhibit no symptoms or insignificant symptoms of a disease. Resistance is: thus preferably the ability of a plant to reduce the development of a pathogen. (see for example Robinson, R.A., 1969: Review Applied Mycology 48, 593-606).

Monogenic: determined by a single locus.

Polygenic: determined by more than one locus.

Dominant: determines the phenotype when present at the heterozygous or homozygous state.

Recessive: only displayed when present at the homozygous state.

Locus: region on a chromosome, which comprises one or more genetic factors, for example one or several genes, contributing to a trait, such as a resistance to a disease.

Genetic linkage: tendency of chromosomal regions to be inherited together as a result of their location on the same chromosome. Measured by percent recombination between loci (centi-Morgan, cM).

Isogenic: plants which are genetically identical, except that they may differ by the presence or absence of a heterologous DNA sequence.

Marker assisted selection: refers to the process of selecting a desired trait or desired traits in a plant or plants by detecting one or more nucleic acids from the plant, where the nucleic acid is associated with the desired trait.

Dihaploid: doubling of haploid (single chromosome) status of the genome (e.g. through anther culture or microspore culture) giving a complete homozygous plant.

"Tester" plant: plant used to characterize genetically a trait in a plant to be tested. Typically, the plant to be tested is crossed with a "tester" plant and the segregation ratio of the trait in the progeny of the cross is scored.

The present invention discloses *B. oleracea* plants resistant to the disease clubroot, more particularly to clubroot disease caused by the pathogen *Plasmodiophora brassicae*. In particular, the present invention discloses *B. oleracea* plants, which comprise a monogenic, dominant resistance to the disease. This resistance provides improved resistance to the disease, when compared to existing resistances in *B. oleracea* and can be easily transferred between *B. oleracea* plants.

*Brassica* species and sub-species are for example described in P. H. Williams (Screening Crucifers for multiple disease resistance, Workshop 1981, Un. Wisconsin-Madison) and have been further genetically analyzed in Song, K M et al. TAG 75, 1988, 784-794; TAG 76, 1988, 593-600 and TAG 79, 1990, 497-506 (Series of 3 articles).

In a preferred embodiment, *B. oleraceas* plants of the present invention are for example: *Brassica oleracea* L. (cole-crops)

var. *acephala* DC. (kales)
var. *albiflora* Sun [=*B. alboglabra*] (Chinese kale)
var. *alboglabra* [=*B. alboglabra*] (Chinese kale)
var. *botrytis* L. (cauliflower, heading broccoli)
var. *capitata* L. (cabbage)
var. *chinensis* Prain (burma sarson)
var. *fimbriata* Mill. (kitchen kale)
var. *fruticosa* Metz. (thousand-head kale)
var. *gemmifera* DC. (brussels sprouts)
var. *gongylodes* L. (kohlrabi)
var. *italica* Plenck. (broccoli, calabrese)
var. *sabauda* L. (savoy cabbage)
var. *sabellica* (collards)
var. *tronchuda* L. H. Bailey (tronchuda cabbage)
var. *costata* (Portugese cabbage)
var. *medullosa* (marrow stem kale)
var. *pamifolia* (kale, Jersey kale)
var. *ramosa* (thousand-head kale)
var. *selensia* (borecole)

Preferred *B. oleracea* plants of the present invention are white cabbage, cauliflower, Brussels sprouts and broccoli.

According to the present invention a monogenic dominant resistance to clubroot is transferred from chinese cabbage (*B. rapa*) to broccoli (*B. oleracea*). Interspecific hybridization is carried out between broccoli (*B. oleracea* var. *italica*) as female parent and *B. rapa* as male parent. Broccoli inbred lines were chosen as female to prevent cell organelles of different origins in the end products of the cross. The male parent in the interspecific cross was a clubroot resistant Chinese cabbage F1 hybrid from Japan, commercially available under the name "Parkin" (Takii Seeds, Japan). After each cross or back-cross, chromosomes of the resulting plants were counted to assess the level of ploidy of the plants and the progress towards obtaining a *B. oleracea* chromosome set. Chromosome counting was carried out according to the method of Chiang et al. (1979) Euphytica 28: 41-45. Flow cytometer work was done with a Partec CA II (Partech, UK).

F1 hybrids resulting from the cross were obtained by embryo rescue. Embryo rescue had to be used since *B. rapa* and *B. oleracea* do not have the same number of chromosomes and are therefore not sexually compatible. Embryo rescue allows to overcome the problems of degradation of the endosperm. The embryo rescue technique described by Harbert et al. (Euphytica 18 (1969) p. 425-429) was used. Sterilized ovules 10-12 days old after pollination are cut in half and introduced to a culture medium kept in constant motion. The culture medium is basically White's medium with 8% sucrose and 400 ppm caseine hydrolysate. The embryo's are washed out of the ovules and grow in the liquid medium.

Clubroot resistant F1 plants were crossed with broccoli (i.e. backcrossed). Embryo rescue as described above was also required to obtain plants resulting from the first back-cross (i.e. BC1 plants).

BC1 plants resistant to clubroot were backcrossed again with broccoli and three clubroot resistant BC2 plants were obtained by normal seed set. Plants are further backcrossed with broccoli and plants resulting from the fourth back-cross (BC4) were used as source of the resistance for other *B. oleracea* crops.

The detailed experimental protocol leading to the transfer of the clubroot resistance to *B. oleracea* is described in Example 1. Disease tests used to test for the presence of the resistance are described in Example 2. Results of field trials demonstrating resistance to clubroot are shown in Example 3.

A representative *B. oleracea* line comprising the monogenic dominant resistance to clubroot according to the present invention, line CFL667, was deposited with NCIMB, Aberdeen AB2 1RY, Scotland, UK under accession number NCIMB 41134 on Jun. 28, 2002. Plants of line CFL667 are a cytoplasmic male sterile line and are heterozygous for the resistance. Accordingly, the resistance to clubroot according to the present invention is obtainable from line CFL667, deposited with NCIMB under accession number NCIMB 41134.

In a preferred embodiment of the present invention, a *B. oleracea* plant resistant to clubroot is defined as a plant assessed at rating 0 or 1 in the 0-5 scale of example 2 herein, or as a plant assessed at rating 1 or 2 in the 1-9 scale of example 2 herein.

The resistance to clubroot was transferred to other *B. oleraceas*, in particular white cabbage, cauliflower and Brussels sprouts, using standard breeding techniques well-known in the *Brassica* art. The trait was also further introgressed into *B. oleracea* elite lines. The introgression of the resistance into the elite line is for example achieved by recurrent selection breeding, for example by backcrossing. In this case, the elite line (recurrent parent) is first crossed to a donor inbred (the non-recurrent parent) that carries the resistance. The progeny of this cross is then mated back to the recurrent parent followed by selection in the resultant progeny for clubroot resistance. After three, preferably four, more preferably five or more generations of backcrosses with the recurrent parent with selection for clubroot resistance, the progeny is heterozygous for the locus harboring the resistance, but is like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376, incorporated herein by reference). Selection for clubroot resistance is carried out after each cross. In a preferred embodiment, the present invention therefore encompasses a method of transferring a dominant and monogenic resistance to clubroot into *B. oleracea* plant susceptible or less resistant to the disease comprising the following steps: crossing a first *B. oleracea* plant with a second *B. oleracea* plant, wherein the first plant comprises a dominant and monogenic resistance to clubroot, selecting a plant resulting from the cross that is resistant to clubroot. A *B. oleracea* plant susceptible or less resistant to the disease is for example rated at level 4 or above, preferably 3 or above, in a test for the disease having a 1-9 scale, or at level 3 or above, preferably 2 and above, in a test for the disease having a 0-5 scale. The method further comprises backcrossing a plant selected above with the second *B. oleracea* plant until the resistance has been transferred to the second *B. oleracea* plant.

The clubroot resistance is preferably transferred to commercial lines of *B. oleracea*. Such lines are for example inbred lines. Alternatively, commercial lines are hybrids, which are obtained by crossing two inbred lines. In this case, the resistance to clubroot may be present in one of the parent inbreds or in both. Therefore, in a preferred embodiment, the present invention discloses an inbred or a hybrid line of *B. oleracea* comprising a monogenic dominant resistance to clubroot, including seeds and materials of said inbred or hybrid and the progeny thereof. Preferably, the resistance is obtainable from a *B. rapa*, preferably from Chinese cabbage F1 hybrid "Parkin". In another preferred embodiment, the resistance to clubroot according to the present invention is present in line CFL667, deposited with NCIMB under accession number NCIMB 41134.

In another preferred embodiment, a clubroot resistant *B. oleracea* plant of the present invention is male sterile. Male sterility is of value in *B. oleracea* hybrid seed breeding because normal flowers are self-pollinating. Male sterile lines do not produce viable pollen and cannot self-pollinate. By eliminating the pollen of one parental variety in a cross, a plant breeder is assured of obtaining hybrid seed of uniform quality. A particularly advantageous male sterility system is cytoplasmic male sterility (CMS). An example of such CMS in *Brassica* is the Ogura CMS originally found in radish (see for example Ogura (1968) Mem. Fac. Agric. Kagoshima Univ. 6: 39-78; Makaroff (1989) Journal of Biol. Chem. 264: 11706-11713; U.S. Pat. No. 5,254,802). Therefore, the present invention discloses a male sterile, in particular CMS, *B. oleracea* plant comprising a monogenic dominant resistance to clubroot, including seeds and materials of said plants and the progeny thereof. Preferably, the resistance is obtainable from *B. rapa*, preferably from Chinese cabbage F1 hybrid "Parkin". Preferably, the CMS is derived from an Ogura genome.

The male fertility of male sterile plants can be restored by methods well-known in the art. The male fertility of CMS plants, in particular CMS *B. oleracea* plants, is preferably restored by cell fusion. For this, cells of a CMS plant are fused to cells of a male fertile plant to replace the nucleus of the fertile plant by the nucleus of sterile plant in the fertile cytoplasmic background, and restore fertility. Cell fusion techniques are well-known in the art and are for example described in Sigareva and Earle (1997) Theor. Appl. Genet.

94: 213-320. Using such techniques, male fertile plants are regenerated, and allowed to self-pollinate or crossed to another plant.

Traits, in particular traits with a scorable phenotype such as a resistance to a disease, can be followed genetically through crosses and the segregation of the trait can be scored in the progeny resulting from the cross. This allows for example to determine whether a trait is dominant or recessive. This also allows to test whether genetic factors for traits are at the same locus (e.g. same gene(s) or different genes, same allele(s) or different alleles) or at different linked or unlinked loci.

For example, when a plant homozygous for a trait is crossed with a "tester" plant homozygous for a dominant trait having the same phenotype, the progeny of the cross does not segregate for the phenotype of the trait (1:0 ratio). This 1:0 ratio is scored when the genetic factors for the trait are at the same locus or at different loci. When the first generation progeny plants of the cross above are self-pollinated, a 1:0 ratio is observed for dominant traits based on genetic factors at the same locus for the plant to be tested and for the "tester" plant. In contrast, a 15:1 ratio is observed for dominant traits based on genetic factors at different, unlinked loci for the plant to be tested and for the "tester" plant. If the genetic factors are at different loci but genetically linked the ratio is generally between these 1:0 and 15:1.

In another example, when a plant to be tested heterozygous for a dominant trait is crossed with a "tester" plant also heterozygous for the dominant trait having the same phenotype, the progeny of the cross segregates 3:1 for the resistant phenotype. This 3:1 ratio is scored when the genetic factors for the trait are at the same locus or at different loci. When the first generation progeny plants of the cross above are themselves crossed with plants of the "tester" line or again with the plant to be tested heterozygous for the trait, a 3:1 ratio is observed for dominant traits based on genetic factors at the same locus, whereas a 23:9 ratio is observed for dominant traits based on genetic factors at different, unlinked loci. If the two genetic factors are at different but genetically linked loci the ratio is generally between these two ratios.

In another preferred embodiment, second generation progenies of individual plants are analyzed separately. In this case, for genetic factors at the same locus, in the second generation 50% of the offspring plants again segregate 3:1, 25% 1:0 and 25% 1:1 when crossed with a heterozygous plant. With an unlinked genetic factor in the plant to be tested, in the second generation, 50% of the offspring plants again segregate 3:1, 25% 7:1, and 25% 1:1 (no plants fixed for the resistance in the second generation).

If the trait is a resistance to a disease and the disease test results in the death of susceptible plants or prevents susceptible plants from flowering, different segregation ratios are scored in the second generation progeny due to the death or lack of progeny of sensitive first generation progeny plants. For example, in this case, instead of 3:1 and 23:9 above, ratios of 5:1 and 19:5, respectively, are observed. If individual plants are scored, second generation progenies are ⅔ 3:1 and ⅓ 1:0 for genetic factors at the same locus, and ⅔ 3:1 and ⅓ 7:1 for genetic factors at different loci.

Other crossing strategies are also used, e.g. with other combinations of homozygous or heterozygous plants, or with plants not comprising the trait. Segregation of the trait in the progeny is then scored. These crossing strategies and their corresponding segregation ratios are well known to the person skilled in the art, who also knows how to obtain and use appropriate "tester" plants, and how to interpret segregation ratios obtained from such crosses.

In another preferred embodiment, the crossing schemes illustrated above are applied to resistance to clubroot disease in the context of the present invention. Accordingly, in another preferred embodiment, the present invention discloses a *B. oleracea* plant homozygous or heterozygous for a resistance to clubroot, wherein when said resistance to clubroot is homozygous in a plant to be tested and said plant to be tested is crossed with a "tester" plant homozygous for a resistance to clubroot, the first generation progeny of said cross shows a 1:0 segregation ratio for the resistance to clubroot. A "tester" plant for such cross is for example a plant derived from line CFL667 deposited with NCIMB under accession number NCIMB 41134 and comprising the resistance of the present invention. In a preferred embodiment, a "tester" plant is derived from a plant of line CFL667 or from a progeny of a plant in line CFL667 by cell fusion. Other male fertile plants comprising the resistance of the present invention can also be used as "tester" plant. In a preferred embodiment, when plants of the first generation progeny are allowed to self-pollinate, the resulting second generation progeny shows a 1:0 segregation ratio for the resistance. In another preferred embodiment, when plants of the first generation progeny are allowed to self-pollinate, the resulting second generation progeny shows a 15:1 segregation ratio for the resistance. In yet another preferred embodiment, a segregation ratio between 1:0 and 15:1 is scored in the second generation progeny after self-pollination. Thus, based on segregation ratios, it is determined whether the resistance of the plant to be tested and the resistance of the "tester" plants are located at the same locus or at different linked or unlinked loci.

In another preferred embodiment, the present invention discloses a *B. oleracea* plant homozygous or heterozygous for a resistance to clubroot, wherein when said resistance to clubroot is heterozygous in a plant to be tested and said plant to be tested is crossed with a "tester" plant heterozygous for a resistance to clubroot, the first generation progeny of said cross shows a 3:1 segregation ratio for the resistance to clubroot. A "tester" plant for such cross is for example a plant of line CFL667 deposited with NCIMB under accession number NCIMB 41134, or a progeny plant of line CFL667 comprising the resistance of the present invention. Any other plant comprising the resistance of the present invention is also used as "tester" plant. In another preferred embodiment, when plants of the first generation progeny are further crossed with plants to be tested heterozygous for the resistance, the resulting second generation progeny are expected to show a 3:1 segregation ratio for the resistance. However, since sensitive plants generally do not survive the disease test for clubroot resistance or are prevented from flowering after such test, the second generation progeny yields a 5:1 segregation ratio. In another preferred embodiment, when plants of the first generation progeny are further crossed with plants of the "tester" line, the resulting second generation progeny are expected to show a 23:9 segregation ratio for the resistance but generally yield a 19:5 segregation ratio. In yet another preferred embodiment, a segregation ratio between 5:1 and 19:5 is scored in the second generation progeny. When progenies of individual plants are separately scored, the ratios described above are observed. Thus, based on segregation ratios, it is determined whether the resistance of the plant to be tested and the resistance of the "tester" plants are located at the same locus or at different linked or unlinked loci.

In yet another preferred embodiment, the present invention discloses molecular markers, which are linked to the monogenic dominant resistance to clubroot. Such molecular markers allow to differentiate at the molecular level between resistant and susceptible plants, and are thus indicative of the monogenic and dominant resistance in *Brassica* plants, preferably *B. oleracea* plants. These molecular markers are based on genetic polymorphisms between resistant and susceptible plants and are located at the locus of the resistance or closely nearby. Molecular markers are for example used to breed and obtain resistant plants, to follow the presence of the resistance during breeding, or to control the presence of the resistance in a commercial seed lot.

Thus, in a preferred embodiment, the present invention provides methods for mapping the clubroot resistance in *Brassica* plants, preferably *B. oleracea* plants, methods for determining whether the resistance is present in a *Brassica* plant, preferably a *B. oleracea* plant, and methods for transferring the resistance to a susceptible or less resistant *Brassica* plant, preferably a *B. oleracea* plant. For example, the methods are used in breeding new resistant plants or lines or to control the quality of a seed lot. The molecular markers disclosed herein allow for quicker release of resistant lines to the market and for a better quality control of commercial seed lots. A disease assay can thus be avoided, and replaced by the use of a molecular marker.

The molecular markers and methods of the present invention are particularly beneficial in the various steps leading to a commercial variety, such as in breeding programs and in the seed production process. For example, the present invention is used to introgress the resistance into a *B. oleracea* plant, for example an elite inbred line. Selection for the resistance to clubroot is carried out by testing seeds or plants resulting from each cross with molecular markers. In a preferred embodiment, the present invention therefore encompasses methods of transferring a dominant and monogenic resistance to clubroot into a *B. oleracea* plant susceptible or less tolerant to the disease comprising the following steps: crossing a first plant resistant to the disease with a second plant susceptible or less resistant, harvesting the seeds resulting from the cross, obtaining a sample of the seed or of a plant grown therefrom, detecting in said sample a molecular marker of the present invention, the presence of said molecular marker being indicative of the resistance to the disease in said seed or plant, selecting a plant positive for the presence of said marker, wherein said plant is preferably resistant to the disease. Preferably, the resistance is then further backcrossed into the susceptible or less resistant plant.

Molecular markers of the present invention are also conveniently used in the production of stable homogenous inbred lines or cultivars (also sometimes called varieties), whereby a particular line is self-pollinated until satisfactory purity and homogeneity of the line is reached. The present invention is similarly used for the commercial production of seeds of a particular line or cultivar. Here again, after each cross a method of the present invention is applied to the seeds resulting from the cross and only resistant plants are selected. In a preferred embodiment, the present invention therefore encompasses methods of producing clubroot resistant seeds or plants comprising the following steps: crossing a resistant plant with itself, harvesting the seeds resulting from the cross, obtaining a sample of the seed or of a plant grown therefrom, detecting in said sample a molecular marker of the present invention, the presence of said molecular marker being indicative of the resistance to the disease in said seed or plant.

Similarly, the present invention is used in hybrid seed production. In this case, the present invention is used to assure that all hybrid seeds that germinate and grow in the field are resistant to the disease. Preferably, molecular markers of the present invention are also used in quality assurance to ensure that the disease resistance is present in the hybrid seeds. In a preferred embodiment, the present invention therefore encompasses methods producing seeds comprising the following steps: crossing a first plant with a second plant, wherein one of the plants is resistant to clubroot, harvesting the seeds resulting from the cross, obtaining a sample of the seed or of a plant grown therefrom, detecting in said sample a molecular marker of the present invention, the presence of said molecular marker being indicative of the resistance to the disease in said seed or plant. The present invention thus provides a significant advancement to commercial breeding and seed production processes.

In a preferred embodiment, a molecular marker of the present invention is within 10 centi-Morgan (cM) from the locus of the clubroot resistance, preferably within 6 cM, preferably within 5 cM, more preferably within 3 cM, even more preferably within 1.5 cM from the locus of the clubroot resistance, and thus tightly co-segregates with the resistance.

Preferred polymorphisms in the context of the present invention include for example single sequence repeats (SSR, see e.g. Hearne et al. (1992) Trends Genet 8:288-294), single nucleotide polymorphisms (SNP, Botstein B et al. (1980) Am J Hum Genet 32:314-331), and any other types of DNA rearrangements, such as deletions, amplifications, crossovers. Methods for detection of polymorphisms well known in the art can be applied in the context of the present invention to produce a molecular marker linked to the resistance. Preferred methods include methods based on the PCR amplification technique, for example the SSR technology and the RAPDs technology (Williams et al. (1990) Nucl Acids Res 18:6531-6535). In general, preferred oligonucleotides for PCR are about 8 to 50 nt long, more preferably 10 to 30 nt long. PCR amplified DNA fragments comprising a site comprising a polymorphism of the present invention are preferably about 100-3,000 nt long, more preferably about 200 to 2,000 nt long, even more preferably about 300 to 1,000 nt long. Other methods for screening or detecting polymorphisms, which are applicable to the instant invention include direct sequencing of nucleic acids, single strand polymorphism assay, ligase chain reaction, enzymatic cleavage, and southern hybridization.

Alternative methods include several methods for detecting Cleaved Amplified Polymorphic Sequences (CAPS; Konieczny et al., The Plant Journal 4(2):403-410, 1993) and for detecting Single Nucleotide Polymorphisms (SNPs) with a method termed "CAMPS" for Cleaved Amplified Modified Polymorphic Sequences, also known as dCAPS (Neff et al, 1998. Plant J. 14: 387-392; Michaels and Amasino, 1998. Plant J 14: 381-385). In the CAPS method, a nucleic acid containing a polymorphic restriction site is amplified using primers flanking the restriction site. The resulting PCR product is digested with the restriction endonuclease corresponding to the polymorphic restriction site, and the digested products are analyzed by gel electrophoresis.

Southern hybridization is also an effective method of identifying differences in sequences, in particular using the RFLP (restriction fragment length polymorphisms) technology (Botstein B et al. (1980) Am J Hum Genet 32:314-331).

In a preferred embodiment, the present invention discloses molecular markers closely linked to the clubroot resistance obtained using the RAPDs technology (see example 4 herein).

The following examples are intended to provide illustrations of the application of the present invention. The following examples are not intended to completely define or otherwise limit the scope of the invention.

All references cited herein are incorporated by reference in the application in their entireties.

EXAMPLES

Example 1

Transfer of the Resistance to *B. oleracea*

F1

A few hundred crosses between the clubroot resistant Chinese cabbage Chinese cabbage F1 hybrid Parkin and broccoli (*B. oleracea*) were performed. From these crosses, embryos were rescued (Harbert et al., Euphytica 18 (1969) p. 425-429). Four of these embryos developed into plants, two of which proved to be resistant to the disease. These two resistant plants had 19 chromosomes. The phenotype was a hybrid between Chinese cabbage and broccoli.

BC1

Embryo rescue was conducted again to obtain BC1 plants. Broccoli inbred lines were used as backcross parent. Broccoli lines were also used a backcross parent for the following generations. Only one of the two F1 plants mentioned above responded and 5 embryos developed into plants. Four of them were resistant to clubroot.

The phenotype of the BC1 plants was closer to that of the broccoli backcross parent.

As the distribution of chromosomes of the *B. rapa* genome in the BC1 plants is at random, the plants contain 18 chromosomes of *B. oleracea* and 0-10 chromosomes of *B. rapa*. Accordingly, plants with 18-28 chromosomes were observed.

BC2

BC2 plants were obtained by seed setting on the BC1 plants. Nine plants originating from seedset on a plant designated as plant B from the BC1 above proved to be resistant to clubroot. The number of chromosomes was determined and the deviation from the normal DNA content was determined with a flowcytometer. Three plants, B23, B27, and B28 were further use in the program.

BC3 and BC4

BC3 and BC4 were also obtained by seed set. Plant B27, which was already diploid in the BC2, had incorporated the dominant clubroot resistance gene. The backcross generations BC3 and BC4 show the expected 1:1 segregation.

The resistance had also introgressed into plants B23 and B28, as was shown in later generations.

Field Test

A preliminary field test was carried out with the resistant plants from the seedling test of the BC3 of B27. The plants were planted in a heavily infested field at our trial station at Kleve, Germany. All plants stayed healthy and showed no symptoms when dug up at maturity.

Transfer to Other *B. oleraceas*

The resistant B27 was used as source of the clubroot resistance for a backcross program in broccoli, cauliflower, cabbage and Brussels sprouts, leading for example to the resistant varieties disclosed in Example 3.

Example 2

Disease Test

Seedlings are transplanted one week after sowing in multipots containing a mixture of sand and peatsoil at a rate of 2:1 with PH<6. One day after transplanting 1 ml of a solution of $1 \cdot 10^6$ cysts/ml is injected in the pots. The solution is of a mixture of clubroot sources with ECD codes 16/3/30, 16/23/30, 16/3/14 and 16/7/30 (Buczacki et al., 1975: Trans. Br. Mycol. Soc. 65, 295-303). The first two weeks the soil is kept wet, after that the soil may dry a bit.

Incubation temp is 18-20° C. in the greenhouse. 4-5 weeks after transplanting the roots are washed clean and scored for the disease.

Alternatively, seeds are directly sown in multipot trays in a standard sand:peat soil mixture (2:1 EGO, pH 5-6, 1 seed per multi-pot). Normally 20-30 plants/line are tested. Approx. 7-10 days after sowing the plants are inoculated, a second inoculation is followed 2-5 days after the first inoculation. If seeds are suspected to germinate badly, sowing is done in black trays on rows and the plants are transplanted after 7-10 days to the multipot trays. Incubation temperature is 20-22° C.

Standard inoculum is isolate 9 (an aggressive isolate isolated from an infected field in Germany). The inoculum is prepared from infected roots stored in the fridge at −20° C. in plastic bags. The roots are transferred to a mixer (1 part roots, 5 parts water) for ca. 2 min. The small particles are then filtered with cheese cloth and the number of cysts (round, light (little blue) coloured) is counted. One ml of $0.5\text{-}1^*10^7$ cysts/ml is added to the stem/root at the base of the plant with a Eppendorf pipet. The inoculum needs to be shaken regularly to mix the available cysts in the suspension homogeneously.

Dependent on the size of the trial, sufficient controls need to be present. Susceptible controls are for example: White Rock (cauliflower), Maximus or other F1 (Brussels sprouts), Marathon (white cabbage). As resistant control Parkin or Storkin (Chinese cabbage) may be added. Hopkin (susceptible Chinese cabbage) may be added, as it gives in an early stage an indication if the inoculation has succeeded.

The plants need to be kept sufficiently moist during the trial. Regular fertilisation necessary, however plants must not grow excessively. Temperature is 22-20° C. (day/night), 16 hr light.

After 4 (summer)-6 (winter) weeks after inoculation plants can be pulled out of the soil, washed and scored for symptoms.

An observation scale for a disease test is for example:
  0=no clubs, healthy root system
  1=1-2 small clubs on lateral roots, sometimes roots show some browning
  2=several small clubs on lateral roots, main root sometimes a little thickened
  3=main root thickened for largest part
  4=main root severely thickened and coalesced with clubbed lateral roots, some normal roots still present
  5=one clump of roots, no normal roots present The plants with score 0 (sometimes also the 1's, depending on the severity of the greenhouse test and the genetics involved) out of the greenhouse test are then transferred to a field infected with clubroot (e.g. field De Wit in Enkhuizen). Normally, escapes from the greenhouse become severely infected in the field and are readily visible (stunted growth). However, these are only very rare plants.

Another observation scale for a disease test is for example:
  1=No visible root galling
  2=Single gall on lateral roots
  3=Several small galls on lateral roots (plant healthy)
  4=Mild galling of the taproot, several small galls on lateral roots
  5=Moderate galling of the taproot, many small or several large galls on lateral roots
  6=Severe galling of the taproot, many large galls on laterals
  7=Severely galled, several healthy roots remaining
  8=Severely galled, few healthy roots present 9=Severely galled, no healthy roots present

Example 3

Results of Field Trials

TABLE 1

Field trial in Werribee, Victoria, Australia. Plants transplanted in January 2002 to clubroot infested soil. An assessment after 6 weeks after transplantation shows (Table 1) already the effect of clubroot resistant cauliflower hybrids according to the present invention (F308 and F311) compared to susceptible varieties (White Rock and Triumphant) and a susceptible variety (Triumphant) treated with different amounts of a fungicide (Shirlane) and addition of lime (increasing pH heaving a reducing effect on clubroot severity, e.g. Dixon & Page, 1998, Acta Horticulturae, 459, 343-349). The observation scale above with rating from 1-9 was used in the trial below.

| | Treatment | Cauli root score 0-9 scale |
|---|---|---|
| 1 | Quicklime (2.5 t/ha) | 4.11 |
| 2 | Shirlan (3 L/ha) | 2.33 |
| 3 | Shirlan (3 L/ha) + Quicklime (2.5 t/ha) | 2.22 |
| 4 | Shirlan (2 L/ha) | 3.00 |
| 5 | Control - Triumphant | 5.06 |
| 6 | F308 | 1.00 |
| 7 | F311 | 1.00 |
| 8 | White Rock | 5.11 |

TABLE 2

Results from a young plant test of cauliflower with isolates originating from 3 different sites in Australia (Cora Lyn, Werribee and Trentham). The isolates were inoculated with a method comparable as described above. White Rock is a susceptible control and E70 is a resistant hybrid cauliflower according to the present invention. The observation scale above with rating from 1-9 was used in the trial below.

| | Treatment averages | | |
|---|---|---|---|
| | Cora Lyn | Werribee | Trentham |
| White Rock | 8.2 | 8.7 | 3.9 |
| E 70 | 1 | 1 | 1 |

TABLE 3

Results of field tests carried out at different locations in Europe naturally infested with clubroot in two years. D249, D506, E245, E246 are resistant cauliflower hybrids according to the present invention, White Rock is a susceptible cauliflower variety, SPR666 and A876 are resistant B. sprouts hybrid according to the present invention, Romulus and Maximus are susceptible B. sprouts varieties, F1182, F1187 are resistant white cabbage hybrids according to the present invention and Marathon a susceptible white cabbage variety. Assessments (di05) were done at the end of the growing season on a 0-5 scale (see above).

| entry | type | site | year | di05 |
|---|---|---|---|---|
| D249 | cauliflower | Hannover | 2000 | 0.0 |
| D506 | cauliflower | Hannover | 2000 | 0.0 |
| White Rock | cauliflower | Hannover | 2000 | 1.8 |
| D249 | cauliflower | Halsall-UK | 2000 | 0.0 |
| White Rock | cauliflower | Halsall-UK | 2000 | 4.3 |
| SPR666 | B. sprouts | Halsall-UK | 2000 | 0.0 |
| Romulus | B. sprouts | Halsall-UK | 2000 | 4.5 |
| SPR666 | B. sprouts | Roeselaere-Belgium | 2000 | 0.0 |
| Romulus | B. sprouts | Roeselaere-Belgium | 2000 | 3.3 |
| A876 | B. sprouts | Halsall-UK | 2001 | 0.0 |
| Maximus | B. sprouts | Halsall-UK | 2001 | 4.5 |
| E245 | cauliflower | Halsall-UK | 2001 | 0.0 |
| White Rock | cauliflower | Halsall-UK | 2001 | 4.6 |
| F1187 | white cabbage | Halsall-UK | 2001 | 0.0 |
| Marathon | white cabbage | Halsall-UK | 2001 | 3.5 |
| E246 | cauliflower | Hannover | 2001 | 0.0 |
| White Rock | cauliflower | Hannover | 2001 | 1.9 |
| F1182 | white cabbage | Hannover | 2001 | 0.0 |
| Marathon | white cabbage | Hannover | 2001 | 3.6 |

Example 4

Molecular Markers

RAPDs markers linked to the resistance were developed using two white cabbage populations (D1544 and D1545). Two molecular markers obtained with primers O20 and Y13, respectively, resulted in PCR amplification products that are tightly linked to the resistance to clubroot. Both O20 and Y13 are 94.6% (53 out of 56) correlated with the result (resistant or sensitive) of disease test in population D1544, indicating a linkage distance of 5.4 cM. For population D1555, O20 is 100% while Y13 is 95.7% (45 out of 47) correlated with disease test, suggesting a tight linkage (0 cM) between O20 and the resistance and 4.3 cM between Y13 and the resistance. When testing the RAPDs in a dihaploid white cabbage population of 140 plants, O20 shows 100% (0 cM) and Y13 98.6% (1.4 cM) correlated with the result of disease tests.

Primer O20 (5'-ACA CAC GCT G-3') yields a specific fragment of approximately 400 bp.

Primer Y13 (5'-GGG TCT CGG T-3') yields a specific fragment of approximately 640 bp.

The amplification conditions are described below. After PCR 25 μl DNA is run on a 1.8% agarose gel.

| | |
|---|---|
| DNA | μl (diluted DNA from a standard miniprep) |
| Primer (10 μM) | 1.0 μl |
| dNTP (2.5 mM) | 2.0 μl |
| Platinum Taq buffer 10x | 2.5 μl (200 mM Tris-HCl pH 8.4, 500 mM KCl minus MgCl$_2$) |
| MgCl$_2$ (50 mM) | 0.75 μl |
| Platinum Taq (BRL/life) | 0.2 μl (5 U/μl) |
| sterile water: | μl (depends how much DNA is used) |
| | 25 μl final volume |

PCR Program:

| | | | |
|---|---|---|---|
| 3' 94° C. | | | |
| Ramp 0:00 94° C. | 0.10 | 1 cycle, PCR cycle (Perkin | |
| Ramp 0:00 36° C. | 0.30 | Elmer 9600) | |
| Ramp 0:45 72° C. | 1.05 | | |
| 3' 94° C. | | | |
| Ramp 0:00 94° C. | 0.10 | 40 cycles, PCR cycle (Perkin | |
| Ramp 0:00 36° C. | 0.30 | Elmer 9600) | |
| Ramp 0:45 72° C. | 1.05 | | |
| 5' 72° C. | | | |

What is claimed is:

1. A method for introgressing a monogenic and dominant resistance to clubroot from *B. rapa* into *B. oleracea* comprising the steps of:
   a) crossing a diploid *B. rapa* plant with a diploid *B. oleracea* plant, wherein said *B. rapa* plant comprises a monogenic and dominant resistance to clubroot;
   b) rescuing embryos resulting from the cross of step a);
   c) regenerating a hybrid F1 plant having 19 chromosomes from an embryo of step b);
   d) selecting a plant of step c) that is resistant to clubroot, wherein the resistance to clubroot is monogenic and dominant;
   e) back-crossing the plant resulting from step d) with a *B. oleracea* plant;
   f) rescuing embryos resulting from the cross of step e);
   g) regenerating a plant having from 18 to 28 chromosomes from an embryo of step f);
   h) selecting a plant of step g) that is resistant to clubroot, wherein the resistance to clubroot is monogenic and dominant;
   i) optionally backcrossing the plant of step h) for one or more generations to a *B. oleracea* plant to produce progeny plants; and
   j) selecting a plant from the later of step h) or step i), wherein said selected plant is a *B. oleracea* plant having 18 chromosomes and comprising a monogenic and dominant resistance to clubroot, thereby introgressing a monogenic and dominant resistance to clubroot from *B. rapa* into *B. oleracea*.

2. The method according to claim 1, further comprising introgreesing the resistance into an elite *B. oleracea* inbred.

3. The method according to claim 2, further comprising crossing said inbred to another *B. oleracea* inbred to produce a hybrid.

4. The method of claim 1 wherein the *B. rapa* plant is Chinese cabbage F1 hybrid Parkin.

* * * * *

SEQUENCE LISTING

```
<160> NUMBER OF SEQ ID NOS: 2

<210> SEQ ID NO 1
<211> LENGTH: 10
<212> TYPE: DNA
<213> ORGANISM: Artificial sequence
<220> FEATURE:
<223> OTHER INFORMATION: Oligonucleotide

<400> SEQUENCE: 1
acacacgctg                                                              10

<210> SEQ ID NO 2
<211> LENGTH: 10
<212> TYPE: DNA
<213> ORGANISM: Artificial sequence
<220> FEATURE:
<223> OTHER INFORMATION: Oligonucleotide

<400> SEQUENCE: 2
gggtctcggt                                                              10
```